(12) United States Patent
Dick et al.

(10) Patent No.: US 11,766,357 B2
(45) Date of Patent: Sep. 26, 2023

(54) DEVICE FOR SUPERIMPOSING PARAMETERS AND/OR IMAGE DATA IN THE STEREOSCOPIC OBSERVATION PATH OF OPHTHALMOLOGICAL DEVICES

(71) Applicant: Carl Zeiss Meditec AG, Jena (DE)

(72) Inventors: Manfred Dick, Gefell (DE); Gerald Kunath-Fandrei, Jena (DE); René Denner, Reisdorf (DE); Thomas Wurlitzer, Leipzig (DE); Rolf Teuscher, Zweibrücken (DE)

(73) Assignee: Carl Zeiss Meditec AG, Jena (DE)

( * ) Notice: Subject to any disclaimer, the term of this patent is extended or adjusted under 35 U.S.C. 154(b) by 598 days.

(21) Appl. No.: 16/652,149

(22) PCT Filed: Sep. 28, 2018

(86) PCT No.: PCT/EP2018/076405
§ 371 (c)(1),
(2) Date: Mar. 30, 2020

(87) PCT Pub. No.: WO2019/063763
PCT Pub. Date: Apr. 4, 2019

(65) Prior Publication Data
US 2020/0268555 A1   Aug. 27, 2020

(30) Foreign Application Priority Data

Sep. 29, 2017   (DE) ...................... 10 2017 217 375.0

(51) Int. Cl.
*A61B 3/00* (2006.01)
*A61F 9/008* (2006.01)
(Continued)

(52) U.S. Cl.
CPC ........ *A61F 9/00821* (2013.01); *A61B 3/0008* (2013.01); *A61B 3/0041* (2013.01);
(Continued)

(58) Field of Classification Search
CPC ....... A61F 9/00821; A61F 2009/00863; A61B 3/0008; A61B 3/0041; A61B 3/14;
(Continued)

(56) References Cited

U.S. PATENT DOCUMENTS 7,836,894 B2   11/2010   Brinkmann et al.
2005/0219552 A1 *  10/2005   Ackerman ......... G01B 11/2536
356/603

(Continued)

FOREIGN PATENT DOCUMENTS

EP   1 217 413 A2   6/2002
EP   2 184 005 A1   5/2010
(Continued)

OTHER PUBLICATIONS

PCT International Preliminary Report on Patentability for PCT/EP2018/076405, dated Apr. 9, 2020, 9 pages.
(Continued)

Primary Examiner — Tuyen Tra
(74) Attorney, Agent, or Firm — DeWitt LLP

(57) ABSTRACT

A device for superimposing parameters and/or image data in the stereoscopic observation path of ophthalmological devices relates to an apparatus for reflecting relevant parameters and/or image data into the stereoscopic observation beam path of ophthalmic devices, for example for therapeutic laser treatments of an eye. The device includes an additional micro-display, which is connected to the control unit, and a beam deflection element for reflecting the parameters and/or image data shown on the micro-display into the stereoscopic observation beam path, which are for example arranged in the parallel beam path. Even though the apparatus is intended for ophthalmic devices for therapeutic laser
(Continued)

treatment in the eye, it can also be used, in principle, for ophthalmic devices for examination, diagnosis and surgical interventions.

19 Claims, 3 Drawing Sheets

(51) Int. Cl.
  *A61B 3/14* (2006.01)
  *G02B 27/09* (2006.01)
(52) U.S. Cl.
  CPC ............ *A61B 3/14* (2013.01); *G02B 27/0977* (2013.01); *A61F 2009/00863* (2013.01)
(58) Field of Classification Search
  CPC ........... A61B 90/20; A61B 3/135; A61B 3/00; G02B 21/22; G02B 21/0012; G02B 27/0977; G16H 20/40; G16H 40/63
  USPC .......................... 606/1, 2; 351/200, 205, 221
  See application file for complete search history.

(56) References Cited

U.S. PATENT DOCUMENTS

| | | |
|---|---|---|
| 2009/0153796 A1 | 6/2009 | Rabner |
| 2014/0228824 A1* | 8/2014 | Yee ..................... A61F 9/00821 606/4 |
| 2014/0361957 A1 | 12/2014 | Hua et al. |
| 2015/0077705 A1 | 3/2015 | Artsyukhovich et al. |
| 2015/0085254 A1 | 3/2015 | Sramek et al. |
| 2015/0157198 A1 | 6/2015 | Sramek et al. |

FOREIGN PATENT DOCUMENTS

| | | |
|---|---|---|
| WO | WO 2012/060724 A1 | 5/2012 |
| WO | WO/14013438 A1 | 1/2014 |

OTHER PUBLICATIONS

International Search Report and Written Opinion for PCT/EP2018/076405, dated Feb. 6, 2019, 15 pages.
English translation of International Search Report for PCT/EP2018/076405, dated Feb. 6, 2019, 3 pages.
Partial Search Report for PCT/EP2018/076405, dated Feb. 6, 2019, 13 pages.
Search Report for DE 10 2017 217 375.0, dated Jun. 4, 2018, 12 pages.
Company brochure; VISULAS 532s von Zeiss; Carl Zeiss Meditec AG; DE_31_010_0022III, printed in Germany CZ-III/2017, 14 pages.
English translation of Company brochure; VISULAS 532s von Zeiss; Carl Zeiss Meditec AG; DE_31_010_0022III, printed in Germany CZ-III/2017, 14 pages.
Company brochure; "VISULAS Trion von Zeiss"; Carl Zeiss Meditec AG; DE_31_010_0006I, printed in Germany CZ-VI/2015, 14 pages.
English translation of Company brochure; "VISULAS Trion von Zeiss"; Carl Zeiss Meditec AG; DE_31_010_0006I, printed in Germany CZ-VI/2015, 14 pages.
Kiire, Christine et al; "Subthreshold Micropulse Laser Therapy for Retinal Disorders"; Retina Today; Jan./Feb. 2011; 67-70.
Landa, Irdex: "Striking Results Achieved with MicroPulse™ Laser Therapy in Patients with Persistent Central Serous Retinopathy" http://www.iridex.com/MicroPulsereg.aspx, pp. 51-53.
OD-OS GmbH: "The Navigated Retina Laser" https://www.od-os.com/de/navilas-laser-system/, 12 pages.

* cited by examiner

DEVICE FOR SUPERIMPOSING PARAMETERS AND/OR IMAGE DATA IN THE STEREOSCOPIC OBSERVATION PATH OF OPHTHALMOLOGICAL DEVICES

RELATED APPLICATIONS

This application is a National Phase entry of PCT Application No. PCT/EP2018/076405 filed Sep. 28, 2018, which application claims the benefit of priority to DE Application No. 10 2017 217 375.0, filed Sep. 29, 2017, the entire disclosures of which are incorporated herein by reference.

FIELD OF THE INVENTION

The present invention relates to an apparatus for reflecting relevant parameters and/or image data into the stereoscopic observation beam path of ophthalmic devices, for example devices for therapeutic laser treatments of an eye.

BACKGROUND

Therapeutic laser therapies of the diseased eye have been integrated into everyday clinical practice for decades. Here, in particular, retinal photocoagulation is an established process for treating various diseases of the fundus, such as diabetic retinopathy or diabetic macular edema. The retina is heated and coagulated by absorption of the laser beam in the retinal pigment epithelium, a layer in the retina that carries a dark pigment (in particular melanin). As a result, the metabolism is focused on the still healthy areas of the retina. Moreover, biochemical cofactors are stimulated. This significantly slows down or stops the course of the disease. Solutions to this end are described in the documents DE 30 24 169 A1 and DE 39 36 716 A1, for example.

In modern laser coagulators such as the Visulas 532s and Visulas Trion by Carl Zeiss Meditec AG, for example, the laser radiation is coupled into a laser slit lamp with the aid of an optical fiber so as then to be applied to the fundus by the physician under stereoscopic observation. As may be gathered from company brochures [1] and [2], the VISULAS 532s with the VITE option can also deliver multi-spot cascades in a fully automatic or manually modified sequence to allow the physician to work more efficiently.

In the case of this therapy, the physician must perform the following tasks, usually even at the same time:
  initially align the laser slit lamp on the patient,
  contact and hold a laser contact glass against their eye so as to provide the optical view, in particular of the retina,
  configure the slit illumination of the laser slit lamp in order to be able to visually optimally capture the areas of the retina to be treated and
  configure the position of the treatment spots with the aid of the pilot beam of the coagulation laser, and
  set the size of the treatment spot.

While the physician is working through these tasks, their gaze is always directed through the binocular eyepiece of the stereomicroscope of the laser slit lamp onto the eye to be treated, a suitable magnification and focusing also having to be selected with the aid of a joystick on the slit lamp.

However, the physician need not only set up the laser slit lamp accordingly, but also still select appropriate laser parameters, such as:
  laser power (mW),
  pulse duration (ms),
  optionally the laser wavelength and
  single shot or pattern.

As a rule, the appropriate laser parameters are set on the display of the laser console. Within this process, a physician considers it particularly time-consuming and annoying to alternately direct their gaze from the binocular eyepiece of the stereomicroscope to the display of the laser console. This can be particularly disadvantageous for spectacle wearers when the diopter compensation is used on the binocular eyepiece, possibly leading to the need for reading glasses to read the display settings.

This should complete the preparations for a treatment. In order to be able to carry out the therapy optimally, however, it is also necessary for the physician to look at diagnostic findings of the patient, such as fundus images, angiography images and OCT scans of the fundus, and "keep an eye" on these. As a rule, these diagnostic findings in the form of images are displayed on another display, to which the physician must also direct their gaze. This, in turn, is associated with the aforementioned disadvantages.

However, the movements of the physician associated with the numerous changes in the direction of view may also lead to the alignment of the laser slit lamp on the patient changing again, and having to be restored before the actual therapeutic treatment.

Consequently, different tasks arise almost simultaneously and there is a great need for making this work environment safer and simpler.

In addition to retinal photocoagulation, other therapeutic laser therapies on the eye also exist on the basis of the known prior art.

While the retina is warmed and coagulated by absorption of the laser beam in the retinal pigment epithelium within the scope of retinal photocoagulation, as "subthreshold micropulse laser therapy" or "MicroPulse®️ laser therapy" and, in particular, "selective retina therapy" (SRT) denote a gentle treatment of the retina, in which there is only a short-term photo-thermolysis of the retinal pigment epithelium without damage to the layer of the photoreceptors in the process. These therapy methods, described in detail in [3] and [4], are based on laser pulses in the ns-µs range and employ the selective and time-limited absorption within the retinal pigment epithelium. Here, in particular, green laser light is used, almost all of the heat of which remains in the selectively absorbing pigment epithelium during the thermal relaxation time (ns-µs) and cannot reach the layer of the photoreceptors. As a result, the damaged pigment epithelium is stimulated to regenerate, without being able to identify any visible damage on the fundus image. A corresponding solution is described in detail in U.S. Pat. No. 7,836,894 B2.

An additional disadvantage in this case is that, in contrast to retinal photocoagulation, no coagulation effect is rendered visible to the physician in the fundus color image during the therapy within the scope of selective retina therapy (SRT) methods. Rather, the physician must therefore very attentively note and register the areas treated on the retina. This is exhausting, even for experienced physicians, in the case of a single spot application, and becomes even more difficult in the case of automated pattern applications.

According to the known prior art, the laser-based treatment methods for diseased eyes include not only therapeutic laser therapies but also laser-based image-guided eye surgery, which has also been integrated into everyday clinical practice for decades.

In addition to a registration unit, a tracking system is also integrated into these image-based laser systems, which makes these systems very complex and expensive in any case. In the system by OD-OS GmbH, described under [5], the stereoscopic view is therefore dispensed with and only a 2D monitor is used for visualization purposes; in principle, this is possible. However, the physician as a result has to make do without information about the 3D situation in the diseased eye during the entire treatment.

EP 2 184 005 A1 describes an image processing method for computer-assisted eye surgery, in particular for the implantation of toric intraocular lenses. Additional information such as the position of the cylinder axis is introduced into a reference image and displayed in the field of view of the surgical microscope during surgery.

WO14013438 A1 describes a system for laser treatment, in which current images of the treatment area are recorded by a camera. By way of an additional image processing unit, existing reference images are transformed onto each digital image of the camera, also provided with one or more graphic features of the reference image, introduced into the microscopic field of view as graphics and overlaid with the live image of the treatment area.

Disadvantageous effects of the solutions for image-based laser systems for eye treatment known from the prior art are that the time and computational expenditure for the preparation is considerable and the systems for introducing the images or graphics, provided with information and data, by reflection are complicated and prone to failure. Moreover, the selection of the information and data to be displayed is too complex and confusing on account of the amount thereof.

US 2015/0085254 A1 describes an illumination system for a slit lamp, said illumination system being based on a micro-display. Here, the micro-display can be self-luminous or comprise an additional illumination source. In addition to a display image, the micro-display also generates an illuminated area and images the latter onto the eye to be examined. By way of example, the display image is a slit that is variable in terms of length and width. However, the micro-display is also able to simultaneously display information such as measurement information, patient data, treatment parameters, preoperative images or a treatment plan. This additional information is reflected by the eye so that the operator recognizes this information.

LITERATURE

[1] Company brochure; "VISULAS 532s von ZEISS; Carl Zeiss Meditec AG; DE_31_010_0022III, printed in Germany CZ-III/2017
[2] Company brochure; "VISULAS Trion von ZEISS"; Carl Zeiss Meditec AG; DE_31_010_0006I, printed in Germany CZ-VI/2015
[3] Kiire, Christine et al; "Subthreshold Micropulse Laser Therapy for Retinal Disorders"; RETINA TODAY; January/February 2011; 67-70
[4] IRDEX: http://www.iridex.com/MicroPulsereg.aspx
[5] OD-OS GmbH: https://www.od-os.com/de/navilas-laser-system/

SUMMARY OF THE INVENTION

Embodiments of the present invention include an apparatus with which therapeutic laser treatments in the eye are substantially simplified for an operator. In the process, movements for changing the viewing direction can be minimized for the operator, making treatment safer and more comfortable as a result. Moreover, the disadvantages of the known solutions of the prior art can be minimized or eliminated by the apparatus.

In the case of the apparatus according to example embodiments of the invention for reflecting relevant parameters and/or image data into the stereoscopic observation beam path of ophthalmic devices, an additional micro-display, which is connected to the control unit, and a beam deflection element for reflecting the parameters and/or image data shown on the micro-display into the stereoscopic observation beam path is present.

Even though the proposed apparatus is intended for ophthalmic devices for therapeutic laser treatment in the eye in particular, it can also be used, in principle, for ophthalmic devices for examination, diagnosis and surgical interventions.

BRIEF DESCRIPTION OF THE DRAWINGS

The invention is described in more detail below on the basis of example embodiments. In this respect.

DETAILED DESCRIPTION

Figure 1:
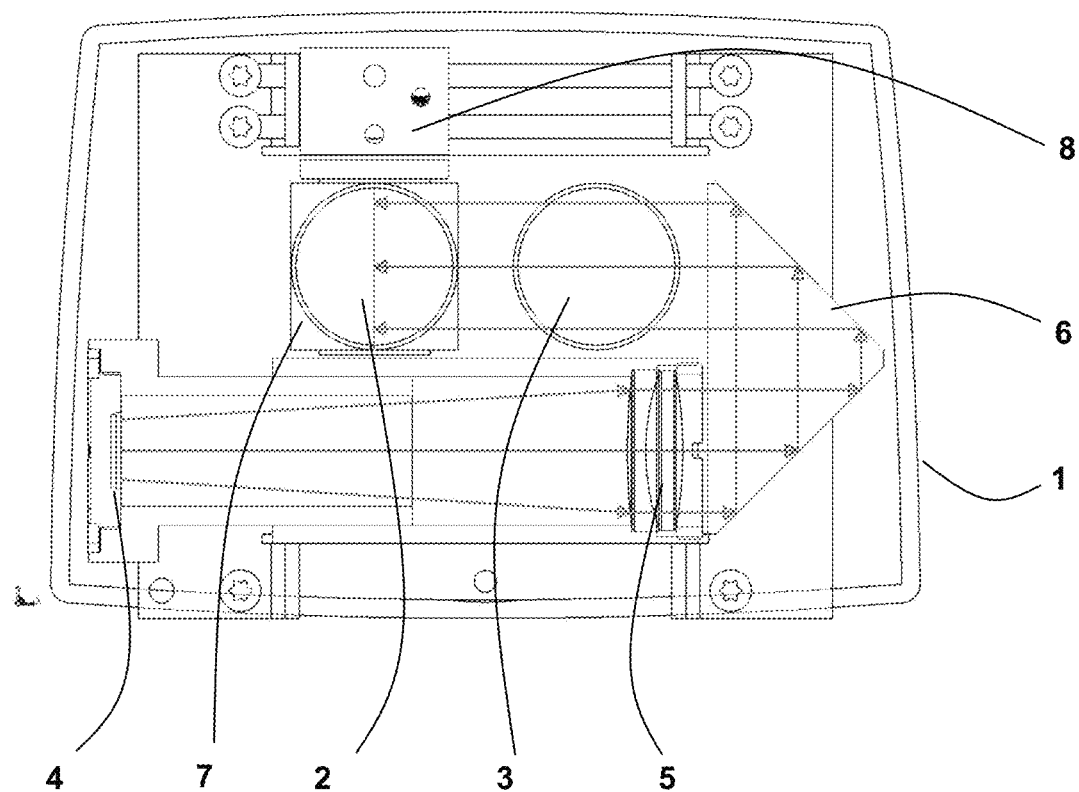
FIG. 1 depicts the arrangement of an apparatus according to the invention in a binocular eyepiece of a laser slit lamp.

The apparatus according to example embodiments of the invention for reflecting relevant parameters and/or image data into the stereoscopic observation beam path of ophthalmic devices includes an additional micro-display, which is connected to the control unit, and a beam deflection element for reflecting the parameters and/or image data shown on the micro-display into the stereoscopic observation beam path, which are for example arranged in the parallel beam path.

The proposed apparatus represents a compact and cost-effective solution for introducing data, parameters and/or images by reflection for diagnostic, therapeutic and surgical ophthalmic devices with a stereomicroscope, which, for example, can be easily integrated into devices with a parallel beam path. Here, the ophthalmic device can be a laser slit lamp, a slit lamp with a link or a binocular laser ophthalmoscope, for example.

In a simple case, a monocular ophthalmic device without 3D visualization, but only 2D visualization, can also be equipped with the apparatus according to the invention for introduction by reflection and a corresponding operating unit.

In accordance with a first advantageous configuration, use is made of micro-displays of the self-illuminating type, the latter preferably having an image diagonal of <1", for example <0.5" and in another example <0.4". The employed micro-displays should have a refresh rate of at least 24, for example more than 50 and in another example more than 100 frames/s, at a resolution of about 1024×768.

According to the invention, semi-transparent mirrors or folding mirrors or prisms are used as the beam deflection element.

A beam deflection element without any spectral reflection or transmission aberrations is provided for a true-color introduction by reflection of the parameters and, for example, images shown on the display.

According to a second example configuration, the beam deflection element for reflecting the parameters and/or image data shown on the micro-display into the stereoscopic observation beam path is arranged in displaceable fashion. This is advantageous in that the parameters and/or image data shown on the micro-display can be selectively coupled into the beam path of the right or left eye of the operator. This allows the visualization to be adapted to the leading (dominant) or non-leading (non-dominant) eye and the associated cognitive visual ability of the operator.

According to a third example configuration, two micro-displays and two beam deflection elements are present for representing and reflectively introducing three-dimensional image data. Here, the display of one micro-display is reflected into the beam path of the right eye and the display of the other micro-display is reflected into the beam path of the left eye of the operator.

In a first display mode, the micro-displays show identical, exactly superimposed image data, and so the operator can register a two-dimensional image with both eyes.

In a second display mode, the same image is presented to the operator in the beam paths of the right and left eyes with an offset, more particularly a lateral displacement, and so the operator can register a stereoscopic image with depth information.

The basis for a spatial image impression of the operator lies in the fact that the human brain, in conjunction with the visual cortex, is able to derive depth information from the smallest lateral position differences of the retinal images supplied by both eyes.

For the first time, it is thus possible to provide an operator, who is making diagnoses with a stereomicroscope and/or who is therapeutically or surgically active, with a further diagnostic, three-dimensional image reflected into the binocular eyepiece, in addition to the stereoscopic live image of the eye provided by the stereomicroscope.

The particular advantage of such an apparatus should be seen in the fact that the operator need you not avert their gaze from the binocular eyepiece in order, for example, to view an important stereo image for performing the examination, therapy or operation, on a separate 3D monitor.

Rather, this apparatus renders it possible to obtain important information "at the push of a button," to be precise without the operator having to change their viewing direction or that of the state of accommodation of their eye.

In addition to the above-described provision of intraoperative information to the operator of a laser slit lamp, this advantage is primarily already effective when operating and, in particular, when changing laser parameters during the treatment. Thus, according to example embodiments of the invention, provision is made for the laser parameters to be able to be varied and activated within predefined ranges by application of adjusting elements at the laser slit lamp the laser parameters via operating elements at the laser slit lamp, such as a multi-functional joystick or an additional rocker or other adjusting elements, and for the provision of visual information to the therapist about these laser parameters to be implemented with the aid of the integrated micro-display according to the invention.

In the configuration variants of the apparatus according to the invention described so far, the beam deflection element or the beam deflection elements is/are arranged in such a way that the parameters and/or image data shown on the micro-display are reflected into the stereoscopic observation beam path in the direction of the operator.

In accordance with a further example configuration, the beam deflection element is embodied in such a way that it can be folded, rotated or displaced by 90° in order to reflect the symbols, structures and/or image data shown on the micro-display into the stereoscopic observation beam path in the direction of the patient. In the case of an appropriate arrangement of two micro-displays and two beam deflection elements, three-dimensional image data can also be displayed and introduced by reflection in this case.

The option of projecting data such as structures, image data or symbols onto the patient's fundus also arises as a result of the use, according to the invention, of self-illuminating micro-displays. To this end, only the deflection direction of the beam deflection elements, which are for example arranged in the parallel beam path, has to be altered; this can be implemented by folding, rotating or displacing.

By way of example, this allows the provision of fixation marks, with and without dynamics, or a structured, spectrally variable illumination for the patient's eye.

Furthermore, during the treatment of the patient, an image or video can be introduced by reflection and projected onto their eye in order to calm said patient. These information items, fixation marks, images or videos that are introduced by reflection for the patient can only be perceived by said patient and do not impair the operator's visual field.

To this end, provision is made, according to example embodiments of the invention, for a structured or homogeneous illumination with an alpha frequency of approximately 11 Hz (8-14 Hz) or with other frequencies, in particular the frequency of human brain waves, to be applied in order to put the patient into a relaxed mood which, under certain circumstances, may result in a state of the patient where they are less sensitive to pain.

According to a further advantageous configuration, the control unit is embodied to actuate the micro-display accordingly in order to present a homogeneous or structured luminous field, structures, signs, parameters, image data, video sequences or the like.

Furthermore, the control unit is embodied to vary, on the basis of the live image of the eye, the color, contrast and brightness of the displays on the micro-display or else to completely mask or switch-off the live image of the eye.

An example configuration, in which an imaging unit and an angle mirror or prism are additionally arranged between a displaceable beam deflection element and a micro-display, is described in more detail below.

To this end, FIG. 1 shows the arrangement of the apparatus according to an example embodiment of the invention in a binocular eyepiece of a laser treatment device, in particular a laser slit lamp.

The binocular eyepiece 1 has the two beam paths 2 and 3 (indicated as circles) for the left and right eye of the operator. The representations generated by the control unit (not shown) on the micro-display 4 are imaged via an imaging unit 5 and an angle mirror 6 onto the beam deflection element 7 (shown as a square) and reflected into the beam path 2 of the left eye of the operator. Here, the beam deflection element 7 can be displaced into the beam paths 3 for the right eye of the operator with the aid of the displacement unit 8.

A micro-display that can be used for the apparatus according to the invention could have the following technical data:
Resolution: 1024×768 (XGA)
Pixel size: 7.6 μm×7.6 μm (sub-pixel 3.8 μm×3.8 μm)
Active area: 7.93 mm×5.99 mm/0.39" diagonal
Luminance: Full color RGB; White: up to 400 cd/m$^2$; 117 fL Contrast ratio: 10 000:1

Video interface. Digital standard (RGB 4:4:4, YCbCr 4:2:2)

Frame rate 24 to 120 frames per second

Power consumption: 200 mW in a typical video mode

Operating temperature: −20° C. to 50° C.

Storage temperature: −30° C. to 70° C.

Thus, according to this example embodiment of the invention, provision is made for the laser parameters to be able to be varied and activated within predefined ranges by means of adjusting elements at the laser slit lamp the laser parameters via operating elements at the laser slit lamp, such as a multifunctional joystick or an additional rocker or other adjusting elements, and for the set laser parameters to be made available to the therapist as visual information items with the aid of the integrated micro-display according to the invention.

Figure 2:
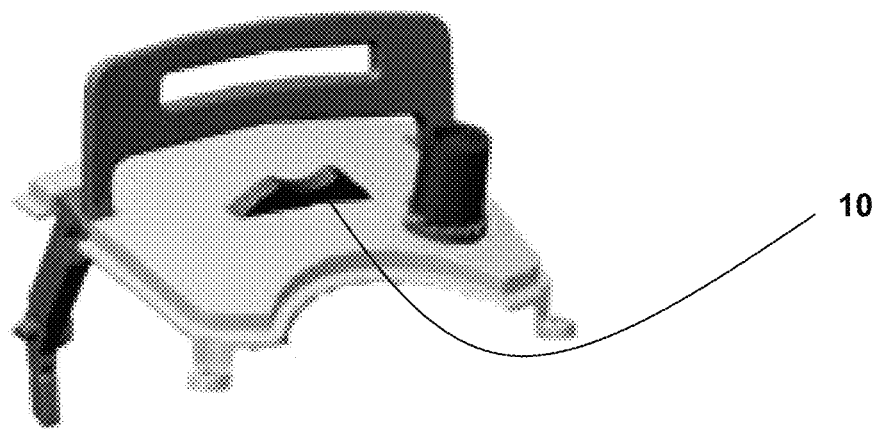
FIG. 2 depicts an operating element to be integrated into a laser slit lamp in the form of a combined jog-rocker switch for selecting and activating laser parameters.

FIG. 2 shows an operating element to be integrated in a laser slit lamp, in the form of a combined jog-rocker switch 10 for the selection and activation of laser parameters. According to this example embodiment of the invention, the respective parameter, such as height, width or spacing of the pulses, is selected by tapping and the value of the respectively selected parameter is decreased or increased by rocking the switch to the left or right.

Figure 3:
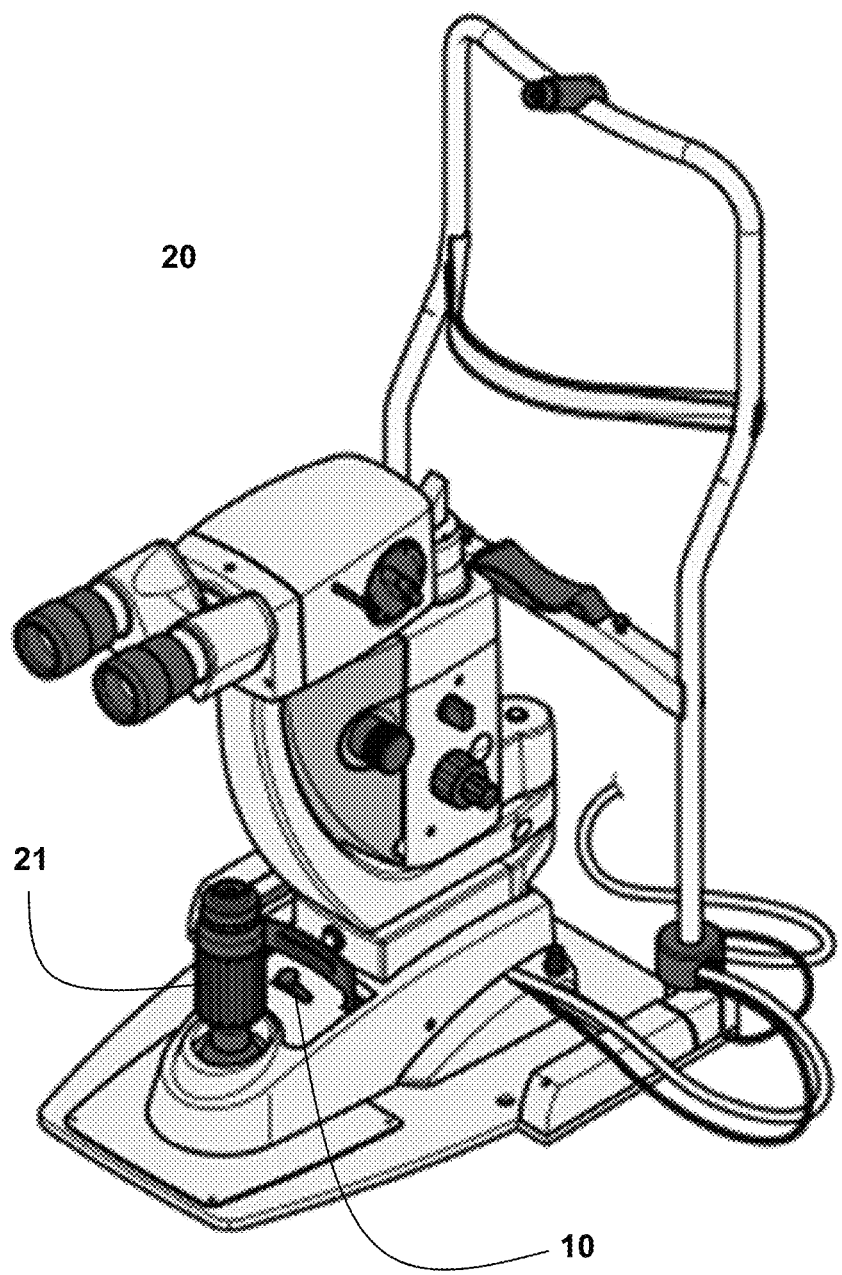
FIG. 3 depicts a laser slit lamp with integrated jog-rocker switch.

To this end, FIG. 3 shows a laser slit lamp 20, in which the combined jog-rocker switch 10 is integrated in the vicinity of the joystick 21. The set laser parameters are displayed with the aid of the integrated micro-display according to this example embodiment of the invention.

Figure 4:
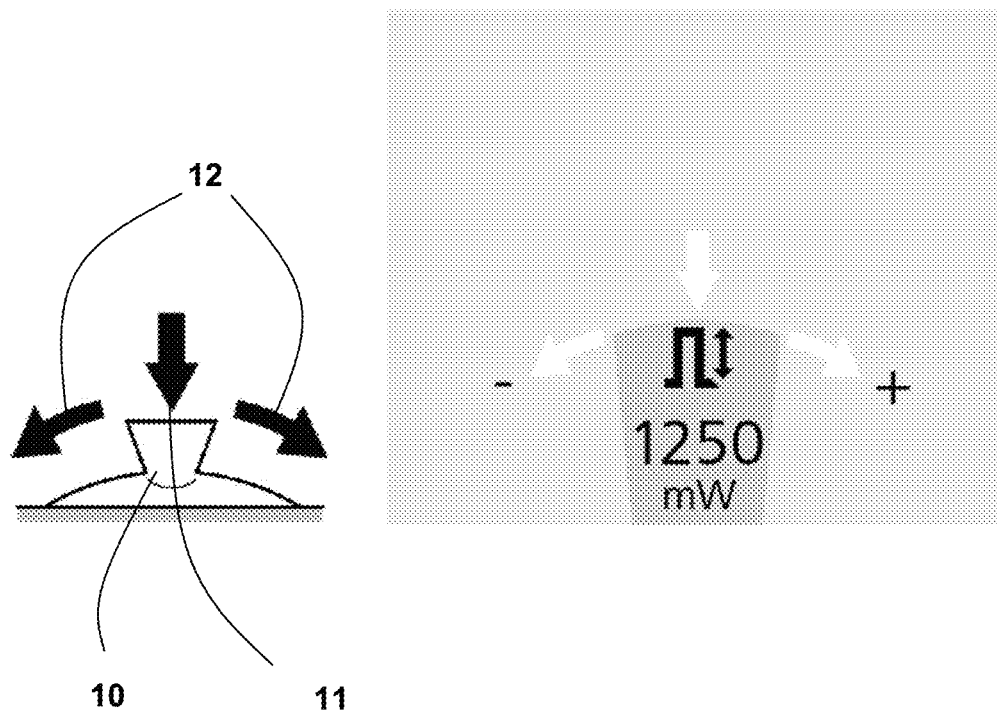
FIG. 4 depicts a jog-rocker switch and a variant for presenting the set parameters and FIG. 5 depicts a live image of the eye to be treated, visible to the operator in the binocular eyepiece of a laser treatment device

FIG. 4 shows a jog-rocker switch and a variant for displaying the set parameters. The left illustration shows that the selection of the respective parameter is set by tapping (arrow 11) the jog-rocker switch 10 and the value of the respectively selected parameter is set by lowering or increasing by way of rocking to the left or right (arrow 12).

The right illustration in FIG. 4 shows a variant for the representation of the set parameters. Accordingly, the pulse height was selected as a parameter and a value of 1250 mW was set using the jog-rocker switch 10.

Figure 5:
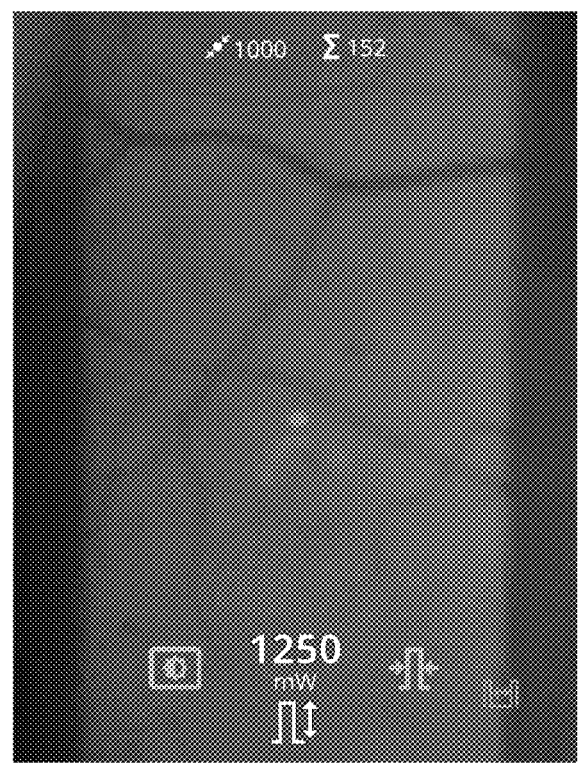

FIG. 5 shows a live image of the eye to be treated, which can be seen by the operator in the binocular eyepiece of a laser slit lamp.

In the displayed live image, the laser spot size and the number of applied laser spots are shown at the top and the display brightness and the laser parameters are shown below. In contrast to FIG. 4, it is not only the selected parameter and the value thereof (pulse height, 1250 mW) that are shown, but also other possible parameters (pulse width and/or pulse spacing).

All of the micro-display configurations described for operators can be used in this case. The operator can be informed about the selection of the laser parameters only via this micro-display having the advantages described, or else in parallel via a display on a conventional operating unit, which is arranged separately from the laser slit lamp.

According to a last advantageous configuration, the control unit is connected to an additional camera that is present for evaluating the live image of the eye and detecting the focusing state.

It is advantageous here for example, if a square optical fiber is used to couple the laser radiation into the treatment device. Simple optical imaging of the fiber end always also renders a square laser spot visible on the retina in the desired focused working state of the laser spot. A magnification can be chosen for the optical imaging of the fiber end. The presence of this laser spot can be detected in the live image of the eye using image processing.

The result of the image processing can then be used as a safety criterion, so that the laser radiation is only released for the treatment if the focusing state is present.

Alternatively, a traffic light can be introduced by reflection for the operator, informing them about the focusing state to thus motivate manual refocusing. In an automated solution, the focus can additionally be adjusted in an automated, motorized manner according to the invention.

Finally, some possibilities of the apparatus according to the invention and the associated advantages are discussed as examples.

As already mentioned, image data and even video sequences can be displayed by the micro-display and reflected into the stereoscopic observation beam path; this can be in addition to symbols and structures.

Forbidden zones for laser therapy, such as the fovea or the optic nerve head, can be detected in conjunction with a camera that records a live image of, e.g., the retina and with appropriate image processing. Markings which, for example, surround these forbidden zones can then be introduced by reflection for the operator. This facilitates so-called "guiding" or treatment guidance during laser treatment with or without a pattern. This can render the implementation of laser therapy safer and more efficient.

In the aforementioned recording of live images, the target beam pointing at potential treatment sites of the retina can be identified and, in the case of laser pattern laser coagulation, a sequential target beam scan can be generated by image processing as a still image on the retina by summing the camera images. This still pattern image can then be displayed in stationary fashion over the potential treatment area of the retina using a display registered to the retina. If the eye moves before the laser therapy radiation is triggered, the pattern shown in the display would still correspond geometrically to the therapy pattern but would be introduced at a different location on the retina if there is no additional tracking system. Therefore, in addition to registering the display image to the live image of the retina, an additional tracking system for correcting the position of the display image on the live image of the retina should also be introduced in this application. In a simple case, the physician has the option of pushing the display image onto the live image of the retina. This is assisted in the case where the display image is sequentially introduced by reflection or in the case of partly transparent display arrangements. If only one display is used for one eye, the physician can always perceive the live image of the retina with the other eye and carry out the displacement for registering both images.

The apparatus also renders it possible to sequentially and/or simultaneously reflect both laser parameters and diagnostic image data into the visual field of the operator for the purposes of observing the eye. In particular, the intensity of the introduction by reflection is adjustable and adapted to the respective illumination situation.

To ensure that the advantages of the device according to the invention also come into play, it must be ensured that the operating elements for setting the parameters of the laser therapy radiation are embodied and/or disposed in such a way that the operator can operate these intuitively. For this, it is advantageous if not only the currently set parameters but also the possible parameters are introduced by reflection as a complete menu.

This is the only way to ensure that the operator can make or change the settings of the laser parameters at the beginning or during the treatment, to be precise without having to avert their gaze from the binocular eyepiece of the ophthalmic device.

To this end, the micro-display should for example display not only status values of the individual system parameters but rather an entire menu guidance for setting all laser control parameters. The display of all selectable parameters puts the operator into a position where they can select the desired parameters directly and not search these sequentially.

However, the operating elements should also allow the display of, e.g., diagnostic data or images during the treatment without the gaze having to be averted from the binocular eyepiece of the stereomicroscope. This allows the operator to constantly keep the patient's eye and, in particular, the areas to be treated in their visual field.

In the example apparatus, the operating device and display for the parameters of the external laser source are integrated in the ophthalmic device. Ultimately, the display of the treatment parameters on the external laser system can thus be dispensed with. In operating theaters, in particular, this has the additional advantage that the surface of an operating display of a laser console, which would otherwise have to be kept sterile, can be dispensed with.

The apparatus furthermore provides for targeted treatment planning for the best possible patient-specific therapy on the basis of diagnostic data. These data can be collected, in particular, on the basis of fundus images (color images, angiography images, autofluorescence images, . . . ), OCT images (optical coherence tomography) or confocally scanned images.

According to example embodiments of the invention, all of the aforementioned image data can also be reflected into the beam path during the treatment. With the aid of the micro-display, these data are presented intraoperatively as full images in sequential fashion and/or in parallel by dividing the image on the display.

As already mentioned above and in contrast to retinal photocoagulation, the procedures of selective retina therapy (SRT) do not reveal any coagulation effect to the operator in the fundus color image during the therapy, and so the operator must therefore note and register the areas treated on the retina very attentively.

The apparatus according to the invention for introducing relevant parameters and/or image data by reflection is also suitable for optimizing selective retina therapy (SRT) methods and for significantly simplifying their implementation for the operator.

An additional camera for recording the live images, e.g., of the retina during the procedure allows the operator to work with precision by virtue of:
  the current situation at the fundus of the patient's eye being recorded by the additional camera, either in the infrared and/or in the visible spectral range,
  the position of the pilot beam being detected with a connected image processing module and being registered with the fundus image at the time when the radiation is triggered,
  the registration being carried out sequentially and summarily, and so a current treatment plan of the fundus is available at any time during the laser therapy, and
  this treatment plan being able to be introduced by reflection by the operator at any time via the micro-display in order to be able to calibrate the further procedure for the application of these invisible laser treatment spots, a choice being available between different image sections or an overview image.

With the solution according to example embodiments of the invention, the operator is provided with an apparatus for reflecting relevant parameters and/or image data into the stereoscopic observation beam path of ophthalmic devices. The apparatus provides particular advantages in devices for therapeutic laser treatment of an eye.

Using the proposed apparatus, the therapeutic laser treatment in the eye is considerably simplified for an operator because movements for changing the viewing direction are minimized for the operator and the treatment becomes safer and more comfortable as a result thereof.

The apparatus described herein represents a very cost-effective and simple solution for introducing relevant parameters and/or image data by reflection. As a result of its compactness, the device can be integrated very well into existing optical arrangements, especially since the available installation space of the system is sufficient in most cases. The solution represents a universally applicable solution for introducing parameters and/or image data by reflection.

Here, what is particularly advantageous is that the operator need not avert their gaze from the binocular eyepiece in order, for example, to view an important stereo image for performing the treatment on a separate 3D monitor. Rather, such image data can be introduced by reflection "at the push of a button" and without the operator having to change their viewing direction or the accommodation state of his eyes.

By way of example, the micro-display can also be controlled in such a way that the ambient illumination is simultaneously darkened or switched off when image data are displayed.

In particular, it is not necessary for the image data introduced by reflection to be registered in advance; this represents a particular advantage in comparison with known solutions from the prior art. Irritations of the operator are avoided by either the image introduced by reflection or the live image being visible.

As a result of the sequential observation of the live image of the fundus and the diagnostic image data of the micro-display, the physician is provided with the opportunity to interpret data information themselves and assign the latter to the live image.

The invention claimed is:

1. An apparatus for reflecting relevant parameters, or image data or both into a stereoscopic observation beam path of ophthalmic devices, comprising:
   a first micro-display, which is operably connected to a control unit, and a first beam deflection element that reflects the parameters or the image data or laser parameters or a combination of the forgoing depicted on the micro-display into the stereoscopic observation beam path wherein the micro-display displays an entire guidance menu of selectable laser control parameters that enables setting all laser control parameters, such that an operator can directly select desired parameters from selectable laser control parameters at a beginning of a treatment or during the treatment.

2. The apparatus as claimed in claim 1, wherein the micro-display and the beam deflection element are arranged in a parallel beam path.

3. The apparatus as claimed in claim 1, wherein the micro-display is self-illuminating.

4. The apparatus as claimed in claim 1, wherein the micro-display has an image diagonal of less than 1".

5. The apparatus as claimed in claim 4, wherein the micro-display has an image diagonal of less than 0.5".

6. The apparatus as claimed in claim 4, wherein the micro-display has an image diagonal of less than 0.4".

7. The apparatus as claimed in claim 1, wherein the micro-display has a refresh rate selected from a group consisting of at least 24 frames per second, more than 50 frames per second and more than 100 frames per second at a resolution of about 1024×768.

8. The apparatus as claimed in claim 1, wherein the beam deflection element further comprises a semi-transparent mirror or folding mirror or a prism.

9. The apparatus as claimed in claim 1, wherein the beam deflection element that reflects the parameters and/or image data shown on the micro-display into the right or left beam path of the stereoscopic observation beam path is arranged in displaceable fashion.

10. The apparatus as claimed in claim 1, further comprising a second micro-display and a second beam deflection element that with the first micro-display and the first beam deflection element represent and reflect three-dimensional image data.

11. The apparatus as claimed in claim 1, further comprising operating elements and wherein the control unit and the operating elements are embodied to modify and activate displayed laser parameters or to select and modify the image data.

12. The apparatus as claimed in claim 1, wherein the ophthalmic device comprises a laser slit lamp and operating elements are arranged at the laser slit lamp by application of a multifunctional joystick, an additional rocker or other adjusting elements that are embodied to modify and activate the displayed laser parameters or to select and modify the image data.

13. The apparatus as claimed in claim 1, wherein the control unit is structured to actuate the micro-display accordingly to display parameters and/or image data.

14. The apparatus as claimed in claim 1, wherein the control unit is structured to vary, on the basis of a live image of an eye, color, contrast and brightness of the parameters and/or image data represented by the micro-display.

15. The apparatus as claimed in claim 1, wherein the control unit is structured to mask or switch off a live image of an eye.

16. The apparatus as claimed in claim 1, further comprising an imaging unit and an angle mirror or prism arranged between the first beam deflection element which is displaceable and the micro-display.

17. The apparatus as claimed in claim 1, further comprising a camera connected to the control unit that enables evaluating a live image of the eye and detecting a focusing state.

18. The apparatus as claimed in claim 1, wherein the first beam deflection element is arranged such that the parameters and/or image data shown on the micro-display are reflected into the stereoscopic observation beam path in a direction of an operator.

19. The apparatus as claimed in claim 1, wherein the beam first deflection element is structured such that the beam first deflection element can be folded, rotated or displaced by 90° to reflect symbols, structures and/or the image data shown on the micro-display into the stereoscopic observation beam path in a direction of a patient.

* * * * *

UNITED STATES PATENT AND TRADEMARK OFFICE
CERTIFICATE OF CORRECTION

PATENT NO. : 11,766,357 B2
APPLICATION NO. : 16/652149
DATED : September 26, 2023
INVENTOR(S) : Manfred Dick et al.

Page 1 of 1

It is certified that error appears in the above-identified patent and that said Letters Patent is hereby corrected as shown below:

In the Specification

Column 4, Line 27, delete "parameters and" and insert --parameters, and--

Column 4, Line 30, delete "device" and insert --device.--

Column 7, Line 1, delete "10 000:1" and insert --10000:1--

Column 7, Line 2, delete "Video interface." and insert --Video interface:--

Column 7, Line 4, delete "Frame rate" and insert --Frame rate:--

Signed and Sealed this
Twenty-eighth Day of November, 2023

Katherine Kelly Vidal
*Director of the United States Patent and Trademark Office*